US00PP32575P2

(12) United States Plant Patent
Wheeler et al.

(10) Patent No.: US PP32,575 P2
(45) Date of Patent: Dec. 8, 2020

(54) BLUEBERRY PLANT NAMED 'BB05-268MI-152'

(50) Latin Name: *Vaccinium corymbosum*
Varietal Denomination: BB05-268MI-152

(71) Applicant: Berry Blue, LLC, Grand Junction, MI (US)

(72) Inventors: Edmund J. Wheeler, Holland, MI (US); James F. Hancock, Scarborough, MI (US)

(73) Assignee: Berry Blue, LLC, Grand Junction, MI (US)

( * ) Notice: Subject to any disclaimer, the term of this patent is extended or adjusted under 35 U.S.C. 154(b) by 0 days.

(21) Appl. No.: 16/602,947

(22) Filed: Dec. 30, 2019

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

*Primary Examiner* — Kent L Bell
(74) *Attorney, Agent, or Firm* — King IP Law; Joshua King

(57) ABSTRACT

A new and distinct cultivar of blueberry plant named 'BB05-268MI-152' as described and shown herein. 'BB05-268MI-152' is a new and distinct high chill tetraploid Northern highbush blueberry (*Vaccinium*) variety consisting of primarily *V. corymbosum*, with a limited contribution of genes from *V. ashei* and *V. darrowi*. 'BB05-268MI-152' is a very productive midseason maturing variety. It is characterized as having large fruit, medium blue in color, and is very firm with a very small and dry picking scar. The fruit is well exposed on a vigorous medium upright bush.

5 Drawing Sheets

Latin name: *Vaccinium corymbosum.*

BACKGROUND AND SUMMARY

Blueberries are a well-known fruit enjoyed by many throughout the world. One example of an existing, patented blueberry variety is 'Bluecrop', unpatented. Another example of an existing, patented blueberry variety is 'Draper', U.S. plant Pat. No. 15,103.

Compared to 'Bluecrop', 'BB05-268MI-152' is more upright, the leaves are much larger in size, the date of 50% ripe fruit is 5 days later and the date of 50% open flowers is 7 days earlier.

Compared to 'Draper', the bush habit of 'BB05-268MI-152' is more spreading, the mature leaf color is lighter green, the berry size and weight are less, the date of 50% ripe fruit is 3 days earlier, the berry is less firm, the date of 50% open flowers is 7 days earlier and 'BB05-268MI-152' has a rounder berry shape.

The present cultivar, 'BB05-268MI-152', provides one or more advantages compared to these and/or other blueberry varieties.

BRIEF DESCRIPTION OF THE PHOTOGRAPHS

DETAILED DESCRIPTION

Figure 1:
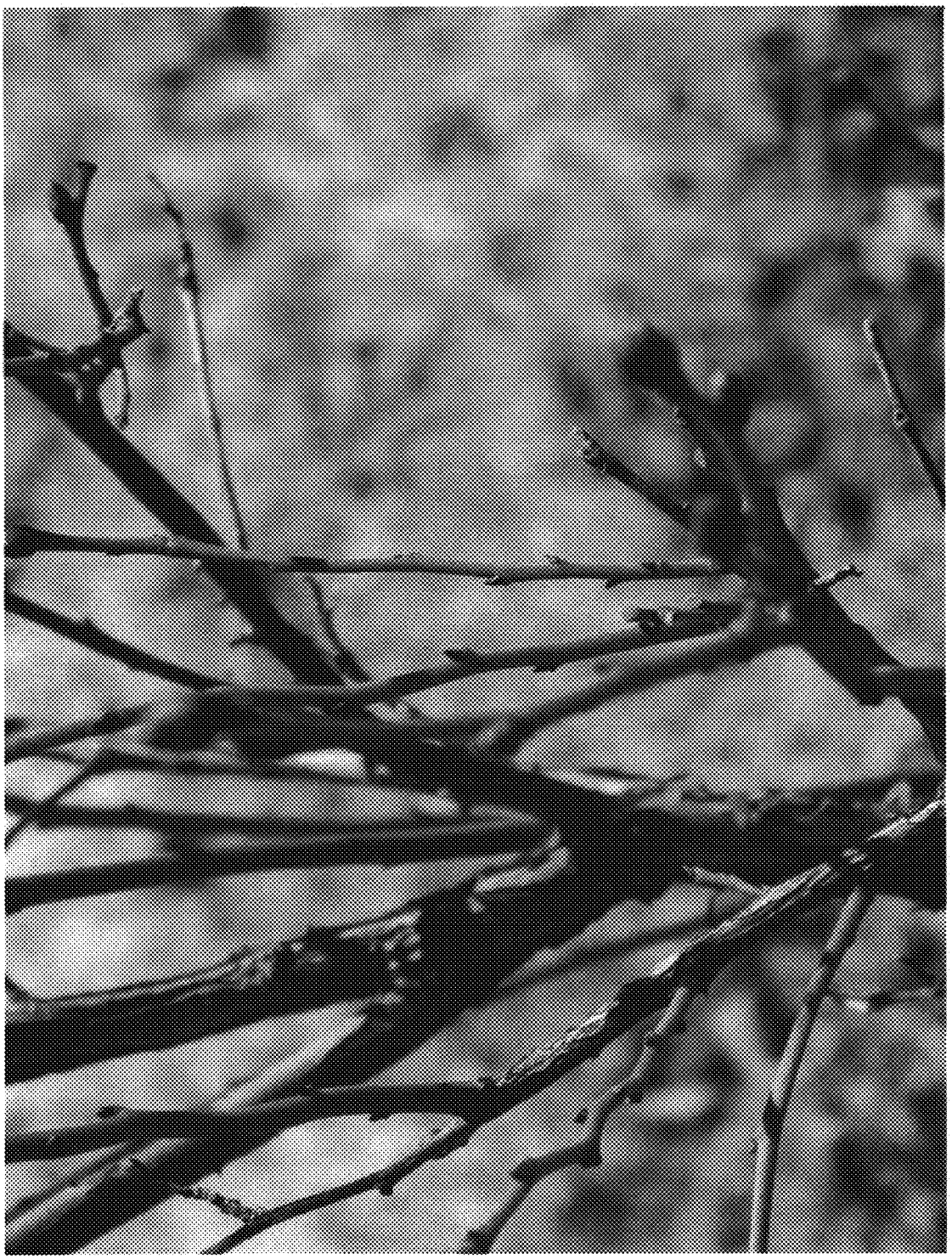
FIG. 1 is a photograph taken in early March 2018, Grand Junction, Mich. of the Blueberry cultivar 'BB005-268MI-152' showing the color of the late winter canes and the color, the size, shape and color of the dormant buds and the color and texture of the older canes.
Figure 2:
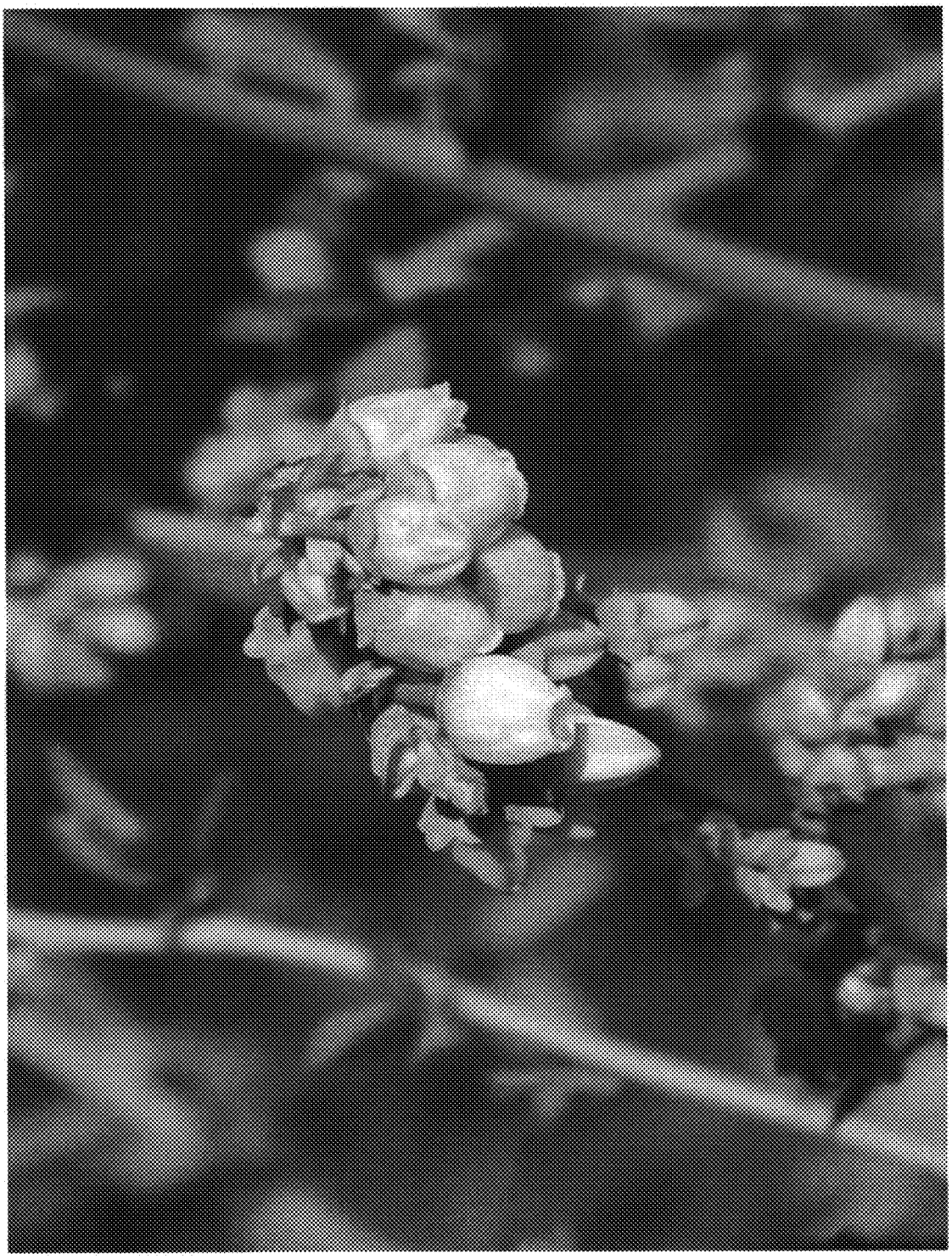
FIG. 2 is a close-up photograph taken in mid-May 2018, Grand Junction, Mich. of the Blueberry cultivar 'BB005-268MI-152' showing unopened flowers, their shape, their color, the color of the peduncles and pedicels.
Figure 3:
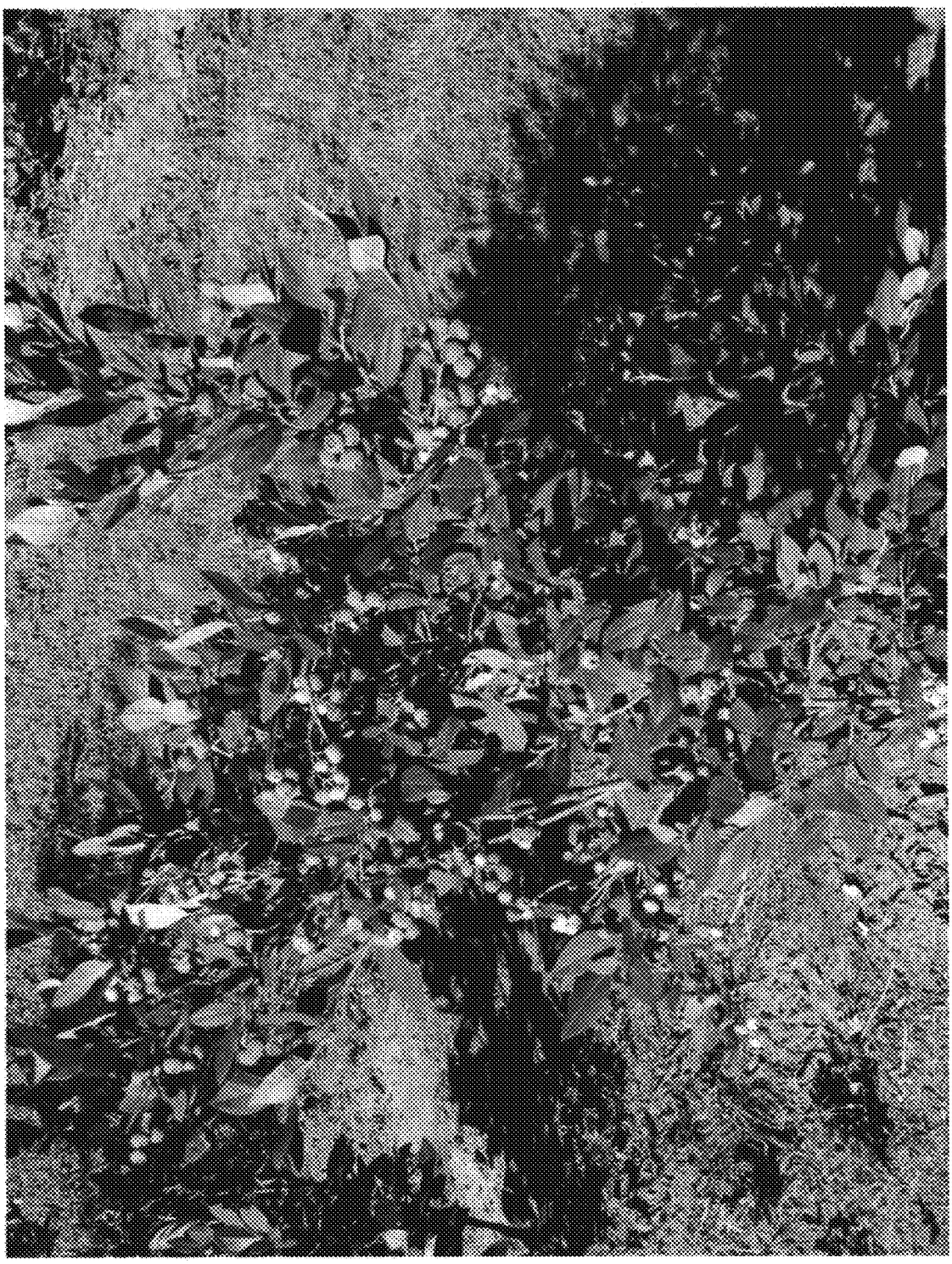
FIG. 3 is a photograph taken in early July 2018, showing of the 6-year-old bush of Blueberry cultivar 'BB005-268MI-152' showing the bush shape, abundance and color of mature leaves, the color of ripe and unripe fruit, and the relative crop load.
Figure 4:
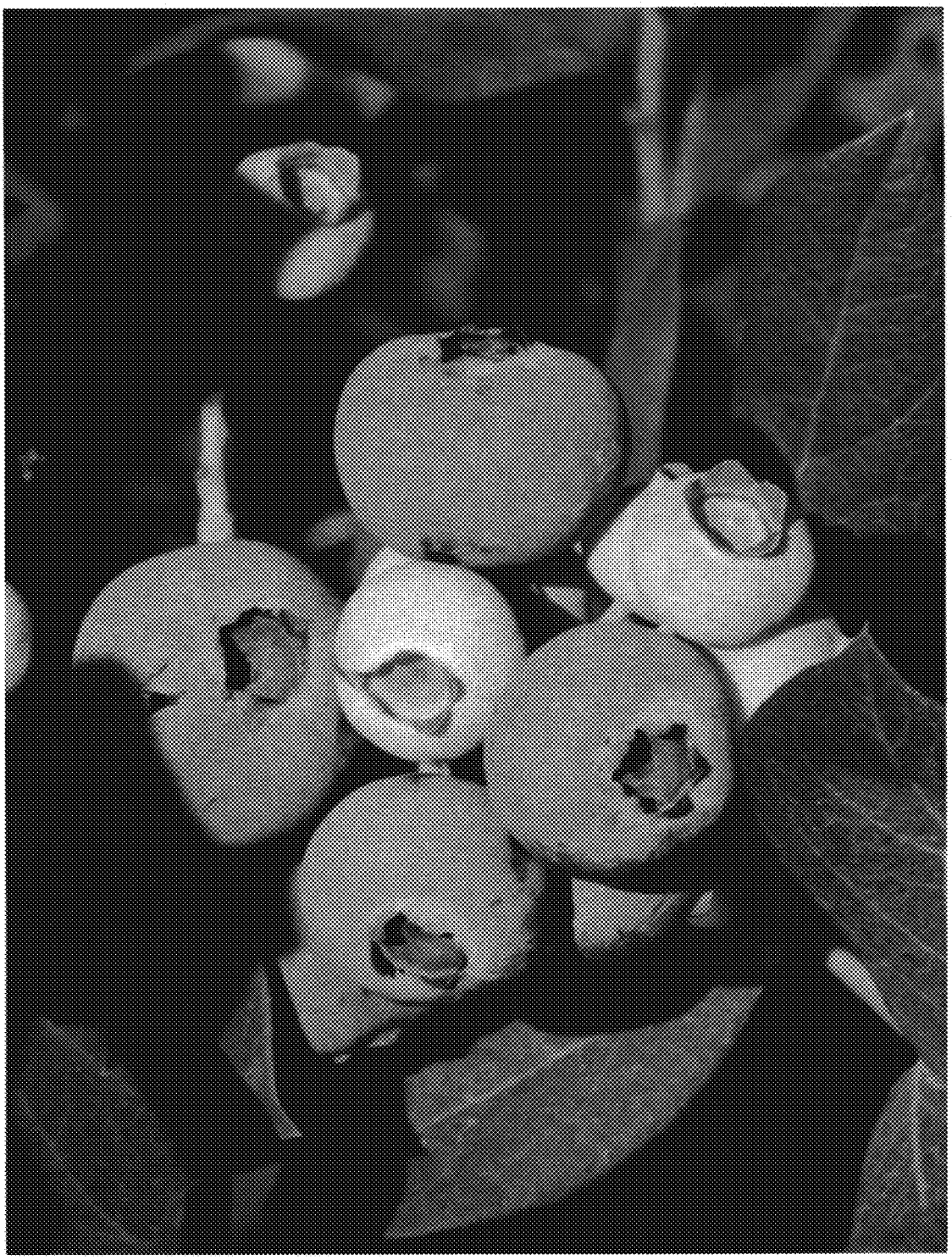
FIG. 4 is a close-up photograph taken in mid-July 2018, Grand Junction, Mich. of the Blueberry cultivar 'BB005-268MI-152' showing ripe and unripe fruit, the shape and relative size and their color, shape and size of the calyx.
Figure 5:
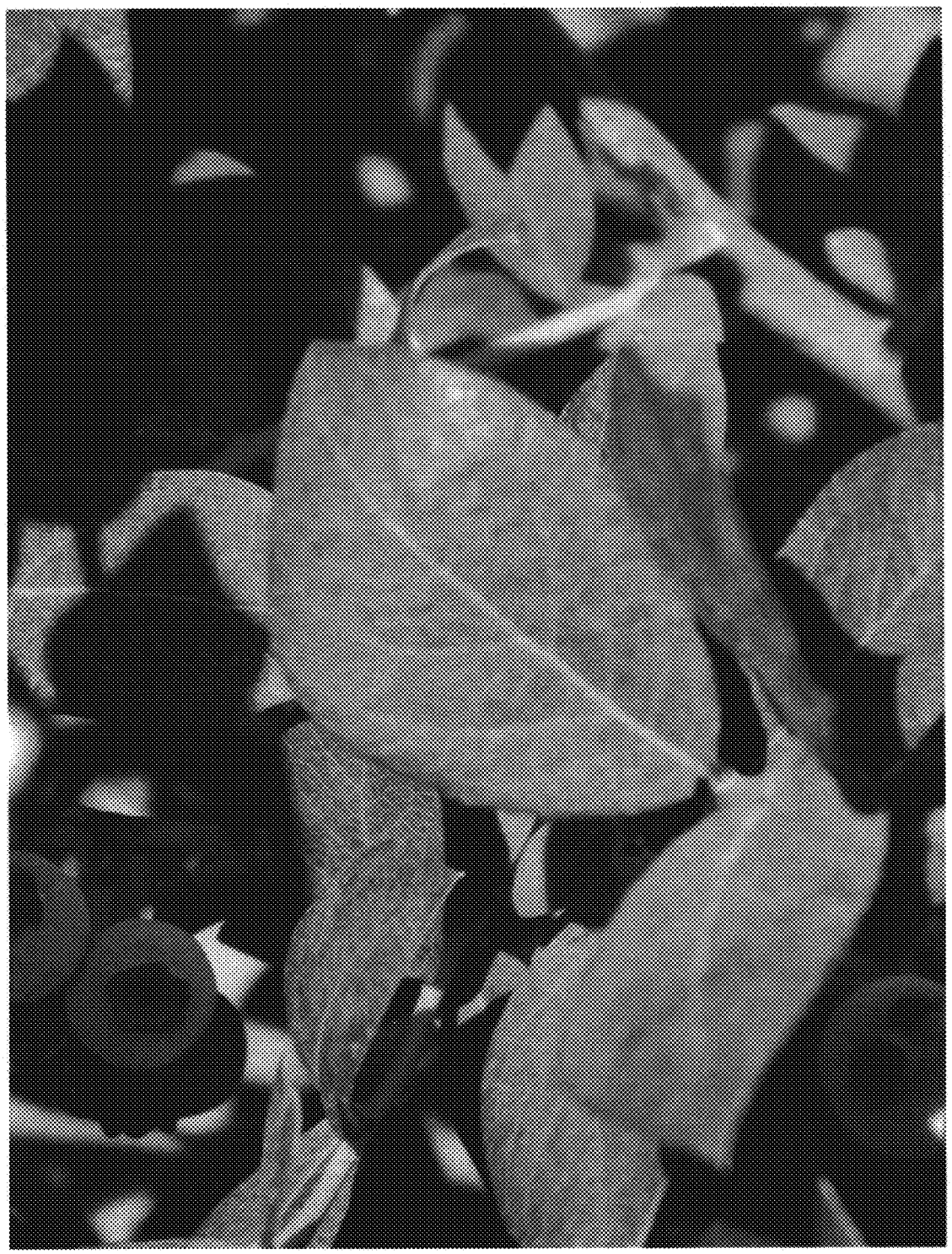
FIG. 5 is a close up photograph taken in early July 2018, Grand Junction, Mich., of the Blueberry cultivar 'BB05-268MI-152' showing the shape, size and color of mature leaves and their venation.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely based on field observations made in 2018 in advanced trial plantings on mature 6-year old bushes in Grand Junction, Mich. Laboratory analysis of fruit characteristics were done in Grand Junction, Mich. in 2018. All progeny have retained the characteristics of the original selection, as appropriate for the various locations cited.

Cultivar Name: 'BB05-268MI-152'.
Classification.
Family: Ericaceae.
Botanical name: *Vaccinium corymbosum.*
Common name: Blueberry.

Parentage.

FEMALE PARENT.

Name: 'Draper'.

USPP: U.S. Plant Pat. No.15,103.

Compared to 'Draper', 'BB05-268MI-152' is more spreading, the mature leaf color is lighter green, the berry size and weight per berry is less, the date of 50% ripe fruit is 3 days earlier, the berry is less firm, the date of 50% open flowers is 7 days earlier and 'BB05-268MI-152' has a rounder berry shape.

MALE PARENT.

'Ozarkblue'.

USPP: U.S. Plant Pat. No. 10,035.

Compared to 'Ozarkblue', 'BB05-268MI-152' has a more upright bush shape, a slightly smaller and lighter colored berry, the date of 50% ripe fruit is 10 days earlier. 'BB05-268MI-152' is a much firmer berry and 'BB05-268MI-152' is slightly sweeter and more acidic. The date of 50% open flowers of 'BB05-268MI-152' is 10 days earlier.

'BB05-268-MI-152' originated as a seedling selected from the cross of 'Draper' (female) x 'Ozarkblue' (male). The seed that gave rise to 'BB05-268MI-152' was produced by hand pollination in a greenhouse in South Haven, Mich. in 2005, grown for 18 months and shipped to Muskegon, Mich. where 'BB05-268MI-152' was planted in an observation nursery in 2007. The plant was evaluated for 3 years and first selected in 2010, based on its excellent fruit and morphological characteristics; i.e. maturity date, bush habit, berry quality, flavor, and storage ability. The bush was given the 'designation 'BB05-268MI-152'. 'BB05-268MI-152' was first asexually propagated by vegetative cuttings in Grand Junction, Mich. in 2010 for additional plantings in 2011. Additional plants have been propagated by softwood cuttings and tissue culture. Five and ten plants were placed in advanced trials in Grand Junction, Mich., South Haven, Mich., Bloomingdale, Mich., and Hammonton, N.J. in 2011 and 2013. All of the propagated plants have retained the original characteristics stated herein, as appropriate for the various locations cited.

'BB05-268MI-152' was first asexually propagated by vegetative cuttings to be used for additional plantings, in 2010 in Grand Junction, Mich. Micropropagation of 'BB05-268MI-152' by tissue culture was first initiated in Middleton, Wisc. in 2013. In all cases, the propagated plants have retained the original characteristics of the original selected plant when grown in Western Michigan or as appropriate for the various locations cited. This variety roots readily from hardwood or softwood cuttings as well as tissue-cultured microshoots.

All field observations were made in 2018 on plants located in advanced trials in Grand Junction, Mich. from plants propagated from the original selected plant. Laboratory analysis of fruit characteristics were done at Grand Junction, Mich. in 2018.

General comments: 'BB05-268MI-152' is a new and distinct high chill tetraploid Northern highbush blueberry (*Vaccinium*) variety consisting of primarily *V. corymbosum*, with a limited contribution of genes from *V. ashei* and *V. darrowi*. 'BB05-268MI-152' is a very productive midseason maturing variety. 'BB05-268MI-152' is characterized as having large fruit, medium blue in color, and is very firm with a very small and dry picking scar. The fruit is well exposed on a vigorous medium upright bush. Along with a small sized crown, a loose fruit cluster, concentrated ripening and very firm fruit that is easily detachable, the variety displays characteristics suitable for mechanical harvest. It is intended for areas that successfully grow high chill Northern highbush varieties. Ripe fruit are large, around 2 grams/berry. The mean date of 50% flowering for BB05-268-152' in Grand Junction, Mich. is May 12. Frost protection may be needed for successful pollination and fruit set. Winter chill requirement for successful flowering and leafing is at least 1000 hours below 7° C. Leaves emerge a few days before flowering commences. The mean 50% ripening date for 'BB05-268MI-152' is about July 11 in Grand Junction, Mich. The fruit shape is oblate with a medium amount of waxy bloom that is rather persistent following handling. It has very good flavor, a balance of sweetness and acidity and is very juicy with a crunchy texture. It has a medium long storage capability of 3 weeks or more in refrigeration with little decline in quality.

References to color refer to The Pantone Book of Color, Eisemann and Herbert, Harry N. Abrams, Inc. Publishers, New York, ISBN 0-8109-3711-5, 1990.

Color measurements were taken with a SpectraMagic NX Model CR410, Konica Minolta, Japan.

Device used to measure Soluble Solids (SS-Brix°), Titratable acidity (TA), pH: PAL-BX/Acid 7, Atago USA, Inc., Bellevue, Wash.

Morphological characteristics reference: Plant Systematics, Jones and Luchsinger, 2 Ed., McGraw Hill, New York, ISBN 0-07-032796-3, 1986.

Firmness readings: BioWorks FirmTec2, Wamena, Kans.

Average size information.

*General description.*—Medium large bush, medium upright bush shape, 5 year old bush averages 120 cm tall, 90 cm wide, height/width ratio — 1.33.

*Growth.*—Very good growth and vigor, leafing is normal and abundant.

*Productivity.*—Very good.

*Cold hardiness.*—Leaf and flower buds −26° C., open flowers and fruit −2° C.

Specific features of the variety.

Plant.

*Growth habit.*—Medium upright.

*Plant width.*—90 cm at mid-bush.

*Plant height.*—120 cm.

*Productivity.*—8.4 lbs. per plant.

*Cold hardiness/tolerance.*—Leaf and flower buds −26° C., open flowers and fruit −2° C.

*Chilling requirement.*—1000+ hours below 7° C.

*Canes.*—Moderately branched, average 5-6 canes per bush, average length of 40cm per cane, range 36-48 cm in length, medium number of lateral branches.

*Mature cane color.*—Pantone Maple Sugar 15-1316.

*Mature cane texture.*—Rough.

*Fruiting wood.*—Immature winter color — Pantone Mineral Red 17-1537, immature summer color — Pantone Willow Green 15-0525.

*Internode length range.*—21-25 mm.

*Surface texture of new wood.*—Smooth.

*Mature canes.*—Circular in shape, mature width 10mm.

*Time of beginning of leaf bud burst.*—April 25, Grand Junction, Mich.

*Time of beginning of flowering.*—May 2, Grand Junction, Mich.

*Date of* 50% *open flowers.*—May 12, Grand Junction, Mich.

*Time of* 50% *fruit ripening.*—July 11, Grand Junction, Mich.

*Disease resistance/susceptibility.*—None claimed.
*Self-fertility.*—Highly self-fertile, pollination by another variety typically results in enhanced berry size and yield.
*Fertility.*—Self-fruitful.

Foliage.
*Leaf color.*—Upper — Pantone Chive 19-0323, Lower — Pantone Spinach Green 16-0439.
*Leaf arrangement.*—Simple Alternate.
*Leaf margins.*—Entire.
*Leaf venation.*—Pinnate.
*Leaf shape.*—Elliptic.
*Leaf apices.*—Acute.
*Leaf bases.*—Acute.
*Typical and observed leaf texture.*—Upper surface: Smooth; Lower surface: smooth except for slight ridging of central vein and lateral veins.
*Vein and petiole coloration.*—Pantone Spinach Green 16-0439.
*Petiole length.*—5 mm.
*Petiole Diameter.*—1.5 mm.
*Petiole color.*—Pantone Grasshopper 18-0332.

Leaf dimensions.
*Overall shape.*—Elliptic.
*Length.*—Range 68-78 mm, average 75 mm.
*Width.*—Range 35-42 mm, average 38 mm.
*Leaf margins.*—Entire.
*Nectaries.*—No nectaries visible on the leaf surface.
*Fall leaf color.*—Pantone Burgundy 19-1617.

Flower buds.
*Shape.*—Elliptic.
*Length.*—6 mm.
*Width.*—2 mm.
*Color.*—Pantone Pompeii 18-1426.

Flowers.
*Flower shape.*—Urceolate.
*Flower bud number.*—Medium high.
*Flowers per cluster.*—Average 8-9 per cluster.
*Flower fragrance.*—Light floral.
*Corolla color.*—Pantone Antique White 11-0105.
*Corolla length.*—7 mm.
*Corolla aperture width.*—4 mm.
*Flower peduncle length.*—3 mm.
*Flower peduncle diameter.*—1 mm.
*Flower peduncle texture.*—Slightly rough.
*Flower peduncle color.*—Pantone Grasshopper 18-0332.
*Flower pedicel length.*—4 mm.
*Flower pedicel diameter.*—1 mm.
*Flower pedicel texture.*—Smooth.
*Flower pedicel color.*—Pantone Grasshopper 18-0332.
*Calyx length* (*with sepals*).—2 mm.
*Calyx color.*—Pantone Spinach Green 16-0439.
*Stamen.*—Length: 5 mm. Number per flower: 10. Filament color: Pantone Hazel 17-1143.
*Style.*—Length 7 mm. Color: Pantone Grasshopper 18-0332.
*Pistil.*—7 mm top of ovary to stigma tip, 1 mm above the top of corolla.
*Ovary color.*—Pantone Grasshopper 18-0332.

Pollen.
*Abundance.*—Moderately abundant.
*Color.*—Pantone Linen 12-1008.

Fruit.
*Date of 50% maturity.*—July 11, Grand Junction, Mich.'
*Duration of ripening;* 17 days.
*Average total yield per plant.*—8.4 lbs per plant.
*Cluster density.*—Loose.
*Berry color with wax.*—Pantone Celestial Blue 14-4308.
*Berry color with wax removed.*—Pantone Majolica Blue 19-4125.
*Berry flesh color.*—Pantone Frozen Dew 13-0513.
*Berry surface wax abundance.*—Moderately heavy, persistent.
*Calyx shape.*—5 point.
*Calyx diameter.*—4 mm.
*Calyx depth.*—1.5 mm.
*Detachment force.*—Easy.
*Berry weight.*—Average 2.0 grams/berry.
*Berry size diameter.*—18 mm.
*Berry height.*—15 mm.
*Typical berry shape.*—Slightly oblate.
*Aspect* (*height/width*).—0.83.
*Average number of fruit per cluster.*—8-9.
*Average fruit weight per cluster.*—16.8 grams.
*Fruit stem scar.*—Small, dry, 1 mm diameter, depth — 0.5 mm.
*Berry firmness.*—Firm; FirmTec2 reading 208 g/mm$^2$.
*Berry sweetness.*—Medium high, Brix°=13.2.
*Berry acidity.*—Medium high, titratable acidity=0.67.
*Berry flavor and texture.*—Balanced flavor of sweetness and acidity, juicy and very crunchy texture.
*Storage quality.*—Excellent, storage of 3 weeks with little loss of quality.
*Suitability for mechanical harvesting.*—A small bush crown, a medium upright bush shape, very firm fruit and easy detachment are desirable for mechanical harvest.

Seed.
*Seed abundance in fruit.*—Average 13 seeds per fruit.
*Seed color.*—Pantone Auburn 18-1343.
*Seed dry weight.*—NA.
*Seed size.*—1 mm length, 0.5 mm width.

Possible typical market uses: Fresh market, processing into jams, purees, and yogurt.

What is claimed is:

1. A new and distinct cultivar of Blueberry plant named 'BB05-268MI-152' as described and shown herein.

* * * * *